United States Patent
Somerville et al.

(10) Patent No.: US 6,897,242 B1
(45) Date of Patent: May 24, 2005

(54) NON-RACEMIC MIXTURES OF D- AND L-METHADONE AND METHOD OF TREATING PAIN

(76) Inventors: Judson J. Somerville, 1503 Trevino Ct., Laredo, TX (US) 78041; Eugene Y. Mironer, 201 English Oak Ct., Spartanburg, SC (US) 29306

( * ) Notice: Subject to any disclaimer, the term of this patent is extended or adjusted under 35 U.S.C. 154(b) by 717 days.

(21) Appl. No.: 09/540,205

(22) Filed: Mar. 31, 2000

Related U.S. Application Data

(63) Continuation-in-part of application No. 09/256,919, filed on Feb. 24, 1999, now abandoned.

(51) Int. Cl.$^7$ ............................................. A61K 31/135
(52) U.S. Cl. ....................................................... 514/648
(58) Field of Search ......................................... 514/648

(56) References Cited

U.S. PATENT DOCUMENTS 6,008,258 A * 12/1999 Inturrisi ...................... 514/648

OTHER PUBLICATIONS

Gorman et al. The d– and l– isomers of methadone bind to teh non–competetive site on the n–methyl–D–aspartate (NMDA) receptor in rat forebrain and spinal cord, Feb. 14, 1997, Neuroscience Letters 223 pp. 5–8.*

Tomoki Nishiyama et al., "Effects of Intrathecal NMDA and Non–NMDA Antagonists on Acute Thermal Nociception and Their Interaction with Morphine", Anesthesiology 1998; pp. 715–722.

J. David Leander et al., "Opioid and Nonopioid Behavioral Effects of Methadone Isomers", The Journal of Pharmacology and Experimental Therapeutics, 1982, vol. 220, No. 3, pp. 592–596.

Naohito Shimoyama et al., "d–Methadone Is Antinociceptive in the Rat Formalin Test", The Journal of Pharmacology and Experimental Therapeutics, 1997, vol. 283, No. 2, pp. 648–652.

George D. Olsen et al., "Clinical Effects and Pharmacokinetics of Racemic Methadone and Its Optical Isomers", Clinical Pharmacology and Therapeutics, 1976, vol. 21, No. 2, pp. 147–57.

John S. Morley, "New Perspectives in Our Use of Opioids", Pain Forum, 1999, vol. 8, No. 4, pp. 200–205.

Y. Eugene Mironer et al., "Successful Use of Methadone in Neuropathic Pain: A Multicenter Study by the National Forum of Independent Pain Clinicians", Pain Digest, 1999, vol. 9, pp. 191–193.

* cited by examiner

Primary Examiner—Marianne C. Seidel
Assistant Examiner—Donna Jagoe
(74) Attorney, Agent, or Firm—Crowell & Moring LLP

(57) ABSTRACT

Compositions of non-racemic mixtures of d- and l-methadone and a method of treating pain using the composition. The composition is especially useful for treating pain of mixed origin. For predominantly neuropathic pain, a mixture of predominantly d-methadone, up to about 90%, is used. For predominantly somatic pain, a mixture of predominantly l-methadone, up to about 90%, is used. The non-racemic mixture of d- and l-methadone may be further combined with a pharmacologically effective amount of a nonopioid component. In another aspect of the invention, the methadone can be combined with an opioid antagonist such as naloxone, naltrexone, or the like.

23 Claims, No Drawings

NON-RACEMIC MIXTURES OF D- AND L-METHADONE AND METHOD OF TREATING PAIN

CROSS-REFERENCE TO RELATED APPLICATION

This application is a continuation-in-part of application Ser. No. 09/256,919, filed Feb. 24, 1999 now Abandoned, which is incorporated herein by reference in its entirety.

BACKGROUND OF THE INVENTION

This invention relates to the treatment of pain and, primarily, this invention relates to drug compositions of nonracemic mixtures of d- and l-methadone and to the treatment of pain and particularly pain of mixed origin using the composition. In another aspect, this invention relates to the treatment of pain using a combination of d-methadone, l-methadone, or a non-racemic mixture of d- and l-methadone and an opioid antagonist such as naloxone, naltrexone, and the like.

Methadone is a well known opioid agonist that is widely used in alleviating chronic pain as well as in treatment of opioid addiction. Methadone, as typically used, is a racemic mixture of the l- and d-isomers. It is well-established that the l-isomer of methadone has mu-opioid activity as well as N-methyl-D-aspartate (NMDA) receptor antagonist activity. It also possesses ability to block re-uptake of noradrenaline and serotonin. Unlike the l-isomer, the d-isomer of methadone has practically no mu-opioid activity, but has NMDA receptor antagonist activity and ability to reverse tolerance to opioid agonists. This is discussed at length in U.S. Pat. No. 6,008,258 to Inturrisi which is incorporated herein by reference in its entirety. U.S. Pat. No. 6,008,258 is primarily concerned with the use of the d-isomer of methadone for the treatment of pain.

U.S. Pat. No. 6,008,258 briefly describes different types of pain, i.e., neuropathic pain, somatic pain, and visceral pain, but makes no distinction in the treatment of these different types of pain. This patent describes treating any type of pain with d-methadone. It is not concerned with the use of l-methadone or with d,l-methadone, the latter of which has already been extensively mentioned in the literature.

The d-isomer of methadone has a longer half-life than the racemic mixture and in doses high enough to provide an effect in animal studies can cause temporary motor paralysis. Administering d-methadone with opioids is difficult because of the significantly longer half-life. It is even worse for intrathecal delivery because it disappears from CSF significantly faster than morphine or hydromorphone. Development of tolerance to d-methadone alone, but not to the non-opioid activity of l-methadone or d,l-methadone has been shown by J. D. Leander & P. E. McCleary, "Opioid and Nonopioid Behavioral Effects of Methadone Isomers," *J. Pharmacol. Exp. Ther.*, 220:592–596, 1982, which is incorporated herein by reference in its entirety.

SUMMARY OF THE INVENTION

While much research has gone into the treatment of different types of pain using different approaches, to the best of our knowledge, neither Inturrisi nor other researchers have recognized that pain may be treated with methadone by varying the proportions of the two isomers. In particular, pain experienced by a patient may be of mixed origin. There may be a component which is neuropathic and a component which is somatic in origin.

Neuropathic pain is pain that results from an abnormal functioning of the peripheral and/or central nervous system. A critical component of this abnormal functioning is an exaggerated response of pain-related nerve cells either in the periphery or in the central nervous system. Somatic pain results from activation of peripheral receptors and somatic sensory efferent nerves, without injury to the peripheral nerve or CNS.

The treatment of pain is not simply prescribing an analgesic. Often, pain is of a particular origin and can be treated as such although, even then a treatment which is effective for one patient may not be effective for another. In many cases, the pain experienced by a patient is of mixed origin —partially neuropathic and partially somatic. The degree of pain which is of neuropathic origin and that which us of somatic origin may vary.

The racemic mixture of methadone does not provide an efficient and effective treatment for pain having both neuropathic and somatic components. The only available adjustment when using d,l-methadone is an increase of the dose. That leads to an excessive amount of a "ballast" isomer for the particular type of pain and that, in turn, leads to decreased results and to a higher level of side effects. Typically, an excess of the d-isomer, for example, will act as a ballast to the effect of the l-isomer, thereby resulting in the need for a higher dosage to obtain the desired effect of the l-isomer.

The present invention is based on the discovery that the d-isomer of methadone is effective in treating neuropathic pain while the l-isomer of methadone is the only effective isomer of methadone for treating somatic pain. Thus, a "cocktail" of different amounts of the d- and l-isomers of methadone tailored to the individual patient is best for treating such pain.

The present invention provides a more effective composition and method of treating pain having both neuropathic and somatic components. This is accomplished by using non-racemic mixtures of varying amounts of d-methadone and l-methadone. In cases where neuropathic pain is predominant, the patient is treated with a composition having a mixture of d-methadone and l-methadone wherein the amount of l-methadone is less than the amount of d-methadone. The mixture could contain up to about 90% d-methadone, the balance being l-methadone. In cases where somatic pain is predominant, the patient is treated with a composition of a mixture of d-methadone and l-methadone wherein the amount of d-methadone in the mixture is less than the amount of l-methadone. The mixture could contain up to about 90% l-methadone, the balance being d-methadone.

Another aspect of the invention is based on the observation that the addition of an opioid antagonist such as naloxone, naltrexone, or the like, to the non-racemic methadone mixture described above, or to racemic dl-methadone or l-methadone eliminates mu-receptor activity. Consequently, when the inventive non-racemic mixture of d- and l-isomers of methadone is administered with Naloxone, thereby eliminating opioid activity, the beneficial mixture of methadone isomers will still react with NMDA, noradrenalin, and serotonin receptors. As a result, the composition can be used for the treatment of pure neuropathic pain.

DETAILED DESCRIPTION OF THE PREFERRED EMBODIMENTS

The composition of the present invention is a non-racemic mixture of d-methadone and l-methadone, with the proportions being tailored to the needs of a particular patient. In one aspect, the inventive method comprises the administration of a non-racemic mixture of d- and l-methadone with each of the two methadone isomers being present in an effective amount to relieve a particular type of pain. In another preferred aspect, the inventive method comprises the administration of a non-racemic mixture of d- and l-methadone with the proportions of the two methadone isomers being adjusted to meet the needs of a particular patient. In yet another aspect of the present invention, naloxone naltrexone, or the like, is administered in an effective amount to eliminate mu-receptor activity with the non-racemic methadone mixture of the present invention or with racemic dl-methadone or l-methadone.

The optical resolution of methadone may be accomplished by any of several methods well-known in the art. For example, through the use of d-tartaric acid. dl-Methadone, or its hydrochloride, may be resolved by forming the easily purified, water-insoluble d-α-bromocamphor-n-sulfonate of the d-isomer. Pure d-methadone is precipitated by slow addition of water. The l-form is obtained, from the mother liquor, by forming the d-tartrate salt.

A method for simultaneous resolution of both optical isomers of dl-methadone is taught in U.S. Pat. No. 2,983,757, which is incorporated herein by reference. The method is based on the knowledge that a seed crystal of the dextrorotatory isomer will attract the d-isomer in saturated solution, and when the degree of saturation of the solute in the solution is increased, the d-isomer will tend to crystallize out on the d-isomer seed crystal. At the same time, a portion of the l-isomer will tend to crystallize out on the l-isomer seed crystal. This process will continue so long as the solution is supersaturated with the composition or solute and seeded crystals will grow to substantial size. At the conclusion of the operation, it will be found that relatively pure crystals of the d-isomer and l-isomer will have been grown on the seed crystals.

The methadone mixture of the present invention may be administered in any form well-known in the art. Administration may be oral (including immediate release and continuous release forms); rectal; parenteral (for example, intravenous, intramuscular, subcutaneous, intraventricular, intrathecal, epidural, intracerebroventricular); transcutaneous, intranasal, sublingual, transbuccal, transsclerol, or intraosseous injection. The composition may be administered by means of a transdermal device such as a patch. Any other well-known means of delivery may be used, it being distinctly understood that the foregoing list is not all inclusive.

The composition will ordinarily be formulated with one or more pharmaceutically acceptable ingredients in accordance with known and established practice. Thus, the composition can be formulated as a liquid, powder, elixir, injectable solution or suspension, etc. Formulations for oral use can be provided as tablets, caplets or hard capsules wherein the pharmacologically active ingredients are mixed with an inert solid diluent such as calcium carbonate, sodium carbonate, calcium phosphate, lactose, talc, or kaolin, or as soft gelatin capsules wherein the active ingredients are mixed with an oleaginous medium, e.g., liquid paraffin or olive oil. Tablets may also include granulating and disintegrating agents such as starch, gelatin, and acacia, and lubricating agents such as magnesium stearate, stearic acid, and talc. Tablets may be coated or uncoated. Inert diluents and carriers which may be used in capsules include, for example, calcium carbonate, calcium phosphate, and kaolin.

Aqueous suspensions can include pharmaceutically acceptable excipients such as suspending agents, e.g., sodium carboxymethyl cellulose, methylcellulose, hydroxypropylmethyl-cellulose, sodium alginate, polyvinylpyrrolidone, gum tragacanth and gum acacia; dispersing or wetting agents such as naturally occurring phosphatide, e.g., lecithin, or condensation products of an alkylene oxide with fatty acids, e.g., polyoxyethylene stearate, or condensation products of ethylene oxide with long chain aliphatic alcohols, e.g. heptadecaethyleneoxycetanol or condensation products of ethylene oxide with partial esters derived from fatty acids and a hexitol, e.g., polyoxyethylene sorbitol monoleate or condensation products of ethylene oxide with partial esters derived from fatty acids and hexitol anhydrides, e.g., polyoxyethylene sorbitan monooleate. The aqueous suspensions can also contain one or more preservatives, e.g., ethyl-or-n-propyl-p-hydroxy benzoate, one or more coloring agents, one or more flavoring agents and one or more sweetening agents, such as sucrose, saccharin or sodium or calcium cyclamate.

The dosage of the composition will vary widely according to a number of factors. The treatment of pain is an art which relies on empirical factors more than the treatment of other types of ailments. Thus, the makeup of the composition will vary as will the dosage. In one preferred embodiment, the composition will contain an effective amount of d-methadone for relieving neuropathic pain and an effective amount of l-methadone for relieving somatic pain. In another embodiment, the non-racemic proportions of the d- and l-isomers of methadone can be predetermined and the composition administered in an amount effective to relieve the patient's pain regardless of the source of the pain. The actual dosages can very widely from about 5 to about 300 mg/day. Depending on the frequency of administration, the amount of each could be from about 1 to about 100 mg per unit dose.

The composition of this invention may optionally include an analgesic of the nonopioid type. Useful nonopioid analgesics include the coal-tar analgesics, in particular, acetaminophen, and nonsteroidal anti-inflammatory drugs (NSAIDs) such as aspirin, diclofenac, diflusinal, etodolac, fenbufen, fenoprofen, flufenisal, flurbiprofen, ibuprofen, indomethacin, ketoprofen, ketorolac, meclofenamic acid, mefanamic acid, naburnetone, naproxen, oxaprozin, phenylbutazone, piroxicam, sulindac, tolmetin, zomepirac, their mixtures and their pharmaceutically acceptable salts.

The composition of this invention may also include a skeletal muscle relaxant or combinations of any of the foregoing. This component may be amobarbital, aprobarbital, butabarbital, mephobarbital, metharbital, methohexital, pentobarbital, phenobarbital, secobarbital, talbutal, theamylal, thiopental and their pharmaceutically acceptable salts and the norbarbiturate sedatives include benzodiazepines having a sedative action such as chlordiazepoxide, clorazepate, diazepam, flurazepam, lorazepam, oxazepam, temazepam, triazolam and their pharmaceutically acceptable salts, $H_1$ antagonists having a sedative action such as diphenhydramine, pyrilamine, promethazine, chlorpheniramine, chlorcyclizine and their pharmaceutically acceptable salts, neuroleptics such as droperidol and miscellaneous sedatives such as glutethimide, meprobamate, methaqualone, dichloralphenazone and their pharmaceutically acceptable salts. Skeletal muscle relaxants may include baclofen, carisoprodol, chlorzoxazone, cyclobenzaprine, methocarbamol, orphrenadine and their pharmaceutically acceptable salts.

In addition to the components already cited, the composition of the present invention can contain one or more other pharmacologically active components, e.g., a stimulant such as caffeine; an antihistamine such as chlorpheniramine maleate; a decongestant such as phenylephrine hydrochloride or phenylpropanolamine hydrochloride; a sympathomimetic such as isometheptene mucate; and/or an anticonvulsant such as gabapentin, phenyloin, carbamazepine, valproate, or clonazepam.

The composition of the present invention is designed to treat a variety of pain conditions, especially chronic pain.

Although the invention has been described with reference to a specific embodiment this description is not meant to be construed in a limiting sense. On the contrary, various modifications of the disclosed embodiments will become apparent to those skilled in the art upon reference to the description of the invention. It is therefore contemplated that the appended claims will cover such modifications, alternatives, and equivalents that fall within the true spirit and scope of the invention.

What we claim is:

1. A composition comprising a non-racemic mixture of l-methadone or a pharmaceutically acceptable salt thereof and d-methadone or a pharmaceutically acceptable salt thereof, and a pharmaceutically acceptable carrier.

2. A composition according to claim 1, comprising a non-racemic mixture of an effective amount of l-methadone or a pharmaceutically acceptable salt thereof to alleviate somatic pain and an effective amount of d-methadone or a pharmaceutically acceptable salt thereof to alleviate neuropathic pain, and a pharmaceutically acceptable carrier.

3. A composition according to claim 1, further comprising a pharmacologically effective mount of an opioid antagonist.

4. A composition according to claim 3, wherein the opioid antagonist is naloxone or naltrexone.

5. A composition according to claim 1, further comprising a nonopioid component and its pharmaceutically acceptable salts.

6. A composition according to claim 1, wherein the amount of l-methadone in said mixture is less than the amount of d-methadone.

7. A composition according to claim 6, wherein the non-racemic mixture of l-methadone and d-methadone contains up to about 90% d-methadone.

8. A composition according to claim 1, wherein the amount of l-methadone in said mixture is more than the amount of d-methadone.

9. A composition according to claim 8, wherein the nonracemic mixture of l-methadone and d-methadone contains up to about 90% l-methadone.

10. A method for treatment of pain in a subject comprising administering the composition of claim 1.

11. A method according to claim 10, wherein said composition is administered orally, nasally, transcuteneously, subcutaneously, intramuscularly, intravenously, intrathecaly or epidurally, sublingually, transbuccally, transsclerolly, or intraosseously.

12. A method according to claim 10, wherein said composition further comprises a pharmacologically effective amount of an opioid antagonist.

13. A method according to claim 12, wherein the opioid antagonist is naloxone or naltrexone.

14. A method according to claim 10, wherein said composition further comprises a nonopioid component and its pharmaceutically acceptable salts.

15. A method according to claim 10, wherein the pain is both neuropathic and somatic in origin.

16. A method according to claim 15, wherein the pain is predominantly neuropathic in origin and the amount of l-methadone in said mixture is less than the amount of d-methadone.

17. A method according to claim 16, wherein the mixture of l-methadone and d-methadone contains up to about 90% d-methadone.

18. A method according to claim 15, wherein the pain is predominantly somatic in origin and wherein the amount of l-methadone in said mixture is more than the amount of d-methadone.

19. A method according to claim 18, wherein the mixture of l-methadone and d-methadone contains up to about 90% l-methadone.

20. A method according to claim 10, wherein the subject is a mammal.

21. A method according to claim 20, wherein the mammal is a human.

22. A method for treatment of pain in a subject comprising administering a composition comprising a mixture of an opioid antagonist and d-methadone or a pharmaceutically acceptable salt thereof or l-methadone or a pharmaceutically acceptable salt thereof to alleviate pain, and a pharmaceutically acceptable carrier.

23. A method according to claim 22, wherein the opioid antagonist is naloxone or naltrexone.

* * * * *